United States Patent
Warberg

(10) Patent No.: US 6,337,081 B1
(45) Date of Patent: Jan. 8, 2002

(54) RODENT REPELLENT SYSTEM

(76) Inventor: Kari G. Warberg, 4551 78th Ave. NW., New Town, ND (US) 58763-9574

( * ) Notice: Subject to any disclaimer, the term of this patent is extended or adjusted under 35 U.S.C. 154(b) by 0 days.

(21) Appl. No.: 09/352,180

(22) Filed: Jul. 12, 1999

(51) Int. Cl.⁷ .............................................. A01N 25/10
(52) U.S. Cl. ...................... 424/417; 424/409; 424/410; 424/411; 424/413; 514/920
(58) Field of Search .................. 514/920, 529, 514/675, 690, 692, 693, 703, 715, 724, 729, 739, 762, 763; 424/405, 406, 409–413, 417, 84, 725, 736, 742, 770

(56) References Cited

U.S. PATENT DOCUMENTS

| | | | | |
|---|---|---|---|---|
| 4,853,413 A | * | 8/1989 | Katz et al. .................. | 514/526 |
| 4,961,929 A | * | 10/1990 | Gurrich et al. .......... | 424/196.1 |
| 5,183,661 A | * | 2/1993 | Messina ..................... | 424/405 |
| 5,356,881 A | * | 10/1994 | Verbiscal .................... | 514/26 |
| 5,364,626 A | * | 11/1994 | Haregawa et al. .......... | 424/403 |
| 5,690,964 A | * | 11/1997 | Hill ............................ | 424/545 |

* cited by examiner

*Primary Examiner*—Neil S. Levy

(57) ABSTRACT

A rodent repellent system for repelling rodents within enclosed areas while simultaneously providing a pleasant scent. The inventive device includes a container having an opening, a drawstring within the opening of the container, cellulose fiber such as corn cob chips, and a fragrance oil. The fragrance oil preferably has a woodsy floral blend similar to potpourri. The container is preferably of a perforated material or cloth. A storage box having a lid preferably stores one or more of the containers preferably within a sealable plastic bag. The user attaches the container to a member within the vehicle such as a handle for retaining the container is a prominent position. The fragrance oil is retained by the corn cob chips and slowly released through the container. The fragrance oil provides a strong scent that repels rodents and small animals by irritating their respiratory system while simultaneously providing a pleasant scent to humans.

1 Claim, 3 Drawing Sheets

RODENT REPELLENT SYSTEM

BACKGROUND OF THE INVENTION

1. Field of the Invention

The present invention relates generally to repellent systems and more specifically it relates to a rodent repellent system for repelling rodents within enclosed areas while simultaneously providing a pleasant scent.

Rodents such as mice and rats are a common problem in enclosed areas. Rodents often infiltrate tractors, trucks, recreational vehicles, boats, implements, and buildings. This is especially true when such devices are in storage for extended periods of time. Rodents can cause significant damage to a vehicle in storage over a period of time. Hence, there is a need for a system that repels rodents while simultaneously providing a pleasant scent for most humans.

2. Description of the Prior Art

Rodent repellent systems have been in use for years. Typically, "mothballs" are utilized within vehicles and clothing in storage. Mothballs are effective in repelling rodents from objects in storage. Unfortunately, mothballs provide an unpleasant scent to most humans that often times remains within the vehicle or clothing.

Another common product utilized to repel rodents from vehicles and other structures are poisonous products such as D-Con. However, poison can be harmful to children if swallowed or touched. In addition, the rodents often times die within the vehicle causing an undesirable odor.

Examples of rodent related devices and system include U.S. Pat. No. 4,735,803 to Katz et al; U.S. Pat. No. 4,775,532 to Clayton; U.S. Pat. No. 5,372,429 to Beaver, Jr. et al; U.S. Pat. No. 4,940,583 to Thompson; U.S. Pat. No. 5,714,445 to Trinh et al; U.S. Pat. No. 5,674,496 to Etscorn et al; U.S. Pat. No. 5,571,522 to Munson et al; U.S. Pat. No. 5,344,649 to Mungia; U.S. Pat. No. 5,242,111 to Nakoneczny et al; U.S. Pat. No. 4,157,696 to Carlberg; U.S. Pat. No. 3,791,346 to Willinger et al; U.S. Pat. No. 5,798,385 to Marin which are all illustrative of such prior art.

While these devices may be suitable for the particular purpose to which they address, they are not as suitable for repelling rodents within enclosed areas while simultaneously providing a pleasant scent. Mothballs provide an unpleasant scent for individuals.

In these respects, the rodent repellent system according to the present invention substantially departs from the conventional concepts and designs of the prior art, and in so doing provides an apparatus primarily developed for the purpose of repelling rodents within enclosed areas while simultaneously providing a pleasant scent.

SUMMARY OF THE INVENTION

In view of the foregoing disadvantages inherent in the known types of repelling systems now present in the prior art, the present invention provides a new rodent repellent system construction wherein the same can be utilized for repelling rodents within enclosed areas while simultaneously providing a pleasant scent.

The general purpose of the present invention, which will be described subsequently in greater detail, is to provide a new rodent repellent system that has many of the advantages of the repelling systems mentioned heretofore and many novel features that result in a new rodent repellent system which is not anticipated, rendered obvious, suggested, or even implied by any of the prior art repelling systems, either alone or in any combination thereof.

To attain this, the present invention generally comprises a container having an opening, a drawstring within the opening of the container, cellulose fiber such as corn cob chips, and a fragrance oil having a woodsy floral blend. The container is preferably of a perforated material or cloth. A storage box having a lid preferably stores one or more of the containers preferably within a sealable plastic bag. The user attaches the container to a member within the vehicle such as a handle for retaining the container is a prominent position. The fragrance oil is retained by the corn cob chips and slowly released through the container. The fragrance oil provides a strong scent that repels rodents and small animals by irritating their respiratory system while simultaneously providing a pleasant scent to humans.

There has thus been outlined, rather broadly, the more important features of the invention in order that the detailed description thereof may be better understood, and in order that the present contribution to the art may be better appreciated. There are additional features of the invention that will be described hereinafter and that will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

A primary object of the present invention is to provide a rodent repellent system that will overcome the shortcomings of the prior art devices.

Another object is to provide a rodent repellent system that effectively repels rodents from structures and clothing.

An additional object is to provide a rodent repellent system that is pleasant smelling to most individuals.

A further object is to provide a rodent repellent system that is a respiratory irritant to rodents and other small animals.

Another object is to provide a rodent repellent system that is has an EPA minimum risk classification to humans.

An additional object is to provide a rodent repellent system that does not harm rodents or humans.

A further object is to provide a rodent repellent system that is easily attachable within a vehicle.

Another object is to provide a rodent repellent system that is comprised of all natural substances.

An additional object is to provide a rodent repellent system that freshens the air within a vehicle.

Other objects and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become fully appreciated as the FIG. 1 is an upper perspective view of the present invention.

DESCRIPTION OF THE PREFERRED EMBODIMENT

Figure 1:
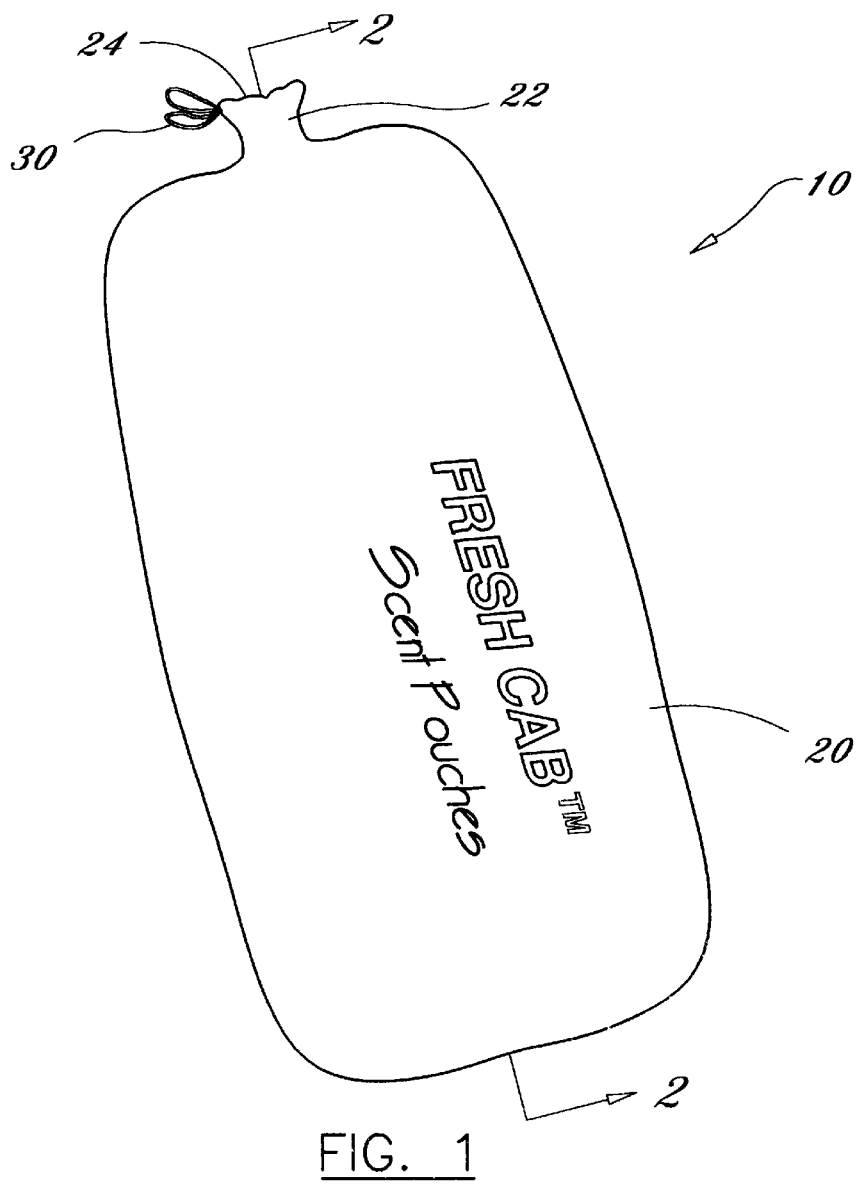

Turning now descriptively to the drawings, in which similar reference characters denote similar elements throughout the several view, FIGS. 1 through 4 illustrate a rodent repellent system 10, which comprises a container 20 having an opening 24, a drawstring 30 within the opening 24 of the container 20, cellulose fiber such as corn cob chips 40, and a fragrance oil having a woodsy floral blend. The container 20 is preferably of a perforated material or cloth. A storage box 50 having a lid 52 preferably stores one or more of the containers 20 preferably within a sealable plastic bag. The user attaches the container 20 to a member within the vehicle 12 such as a handle for retaining the container 20 is a prominent position. The fragrance oil is retained by the corn cob chips 40 and slowly released through the container 20. The fragrance oil provides a strong scent that repels rodents 14 and small animals by irritating their respiratory system while simultaneously providing a pleasant scent to humans.

As best shown in FIG. 1 of the drawings, the container 20 is preferably cylindrical in shape, however it can be appreciated by one skilled in the art that the container 20 may have any well-known shape. The container 20 is constructed of a permeable material such as perforated plastic or cloth.

Figure 2:
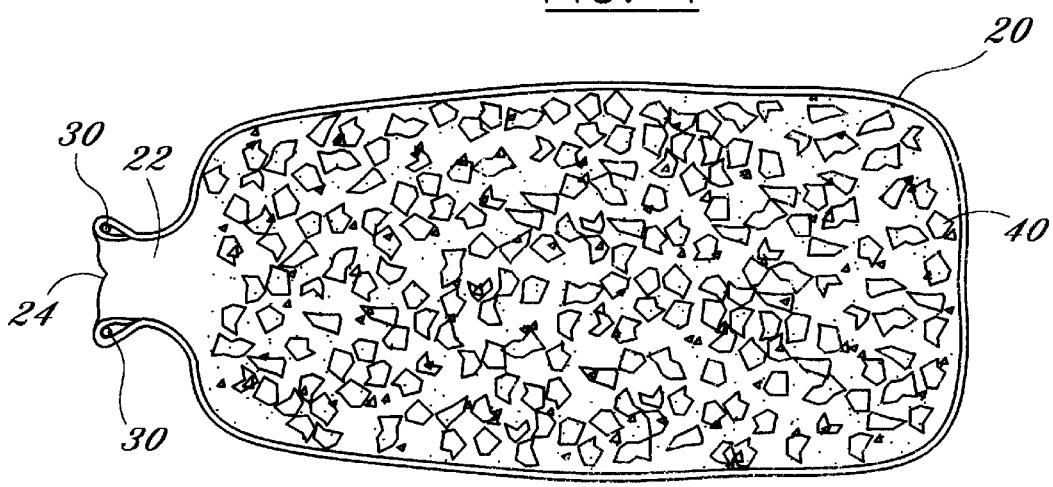
FIG. 2 is a cross sectional view taken along line 2—2 of FIG. 1.
Figure 3:
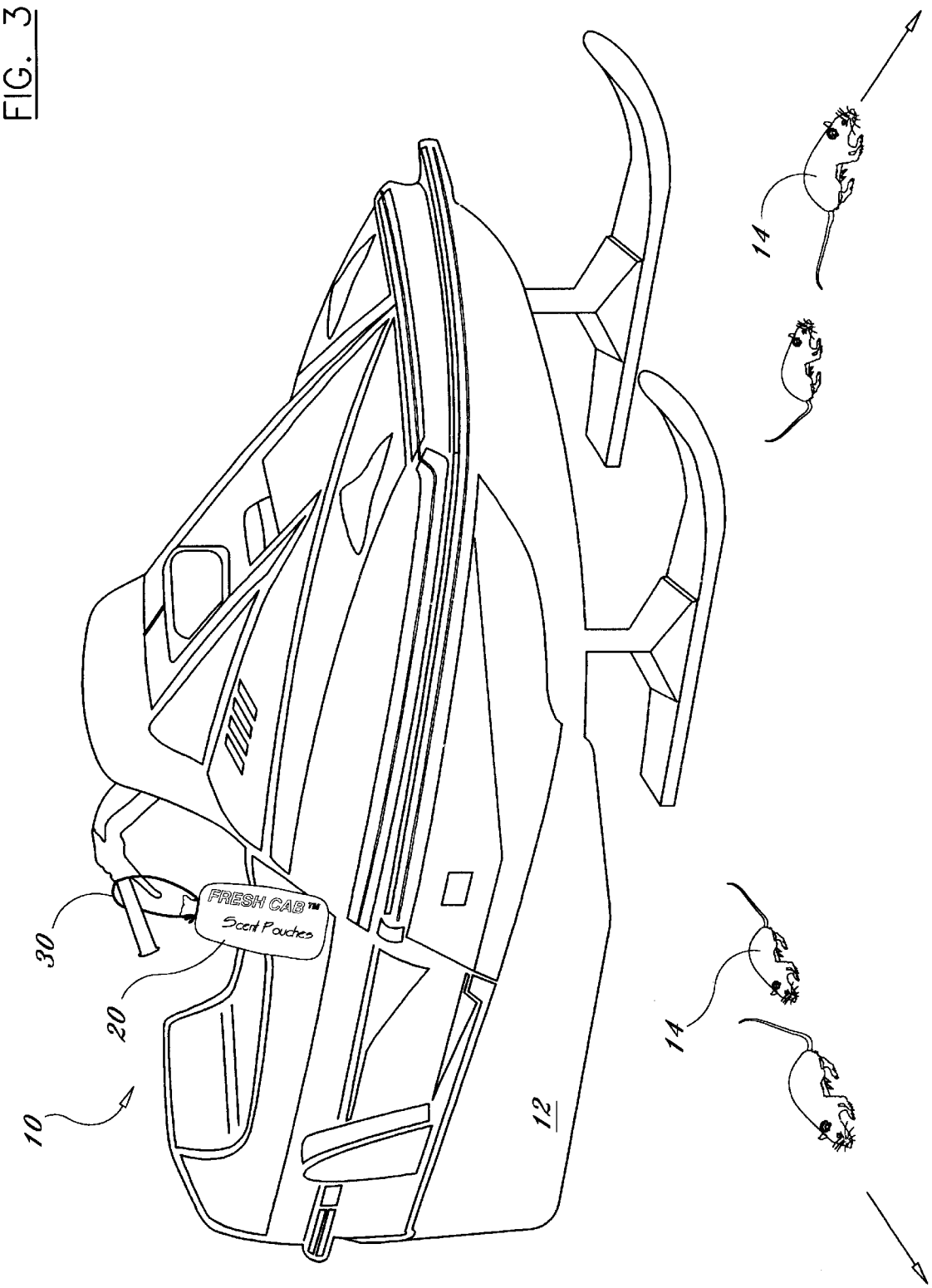
FIG. 3 is an upper perspective view of the present invention attached to a snowmobile.

As best shown in FIGS. 1 and 2 of the drawings, the container 20 includes a neck 22 having an opening 24. A drawstring 30 is slidably positioned within the neck 22 of the container 20 as shown in FIGS. 1 and 2 of the drawings. The drawstring 30 tightens the neck 22 for closing the container 20 while simultaneously providing at least one loop to attach to a handle or other object within a vehicle 12 as shown in FIG. 3 of the drawings.

As shown in FIG. 2 of the drawings, a plurality of material 40 is positioned within the container 20. The material 40 is preferably an absorbent fiber substance such as corn cob chips 40. Other types of absorbent material may also be utilized.

A fragrance oil is mixed into the material 40 so as to be substantially absorbed into the material 40 to be dissipated later over a period of time through the container 20. The fragrance oil preferably has a woodsy floral blend. A suitable product is manufactured by Lebermuth Company that has a woodsy floral scent. The fragrance oil preferably provides a strong scent yet lasts a significant amount of time. Lebermuth Company manufactures several fragrance oils having woodsy floral blends (www.lebermuth.com) wherein these fragrance oils are incorporated by reference for the purpose of providing support to identify and how to provide a fragrance oil having a woodsy floral blend. In addition, the woodsy floral blend of the fragrance oils may be comprised by combining two or more of the fragrance oils manufactured by Lebermuth Company such as but not limited to CANADIAN WILDERNESS FRAGRANCE OIL (Item #8238-01), PLEASANT PINE FRAGRANCE OIL (Item #8228-01) and FLORAL BOUQUET FRAGRANCE OIL (Item #8040-01). CANADIAN WILDERNESS FRAGRANCE OIL (Item #8238-01) is comprised of linalool 90, eucalyptus 80/85, rosemary Spanish, patchouli, turpentine rectified, caryophellene B, acetaldehyde, aldehyde C-14, fir balsam anhydrol, linalyl acetate special, dioctyl adipate, cis 3 hexenyl acetate, mousse de chene, hydroxy citronellal, iso borneol acetate, neryl acetate, fir balsam, viridine, fir needle Canadian, galaxolide 50, musk ketone, boreol leavo, hercolyn D, benzyl salicylate, camphor gum, grapefruit white, sage clary, mousse de arbre, styrallyl alcohol, vertenex, cedarwood Texas white, lemon California, veltol plus and fenchyl alcohol alpha. In addition, WINDSONG BALSAM PINE FRAGRANCE OIL (Item #7225-01) may be utilized within the present invention.

Figure 4:
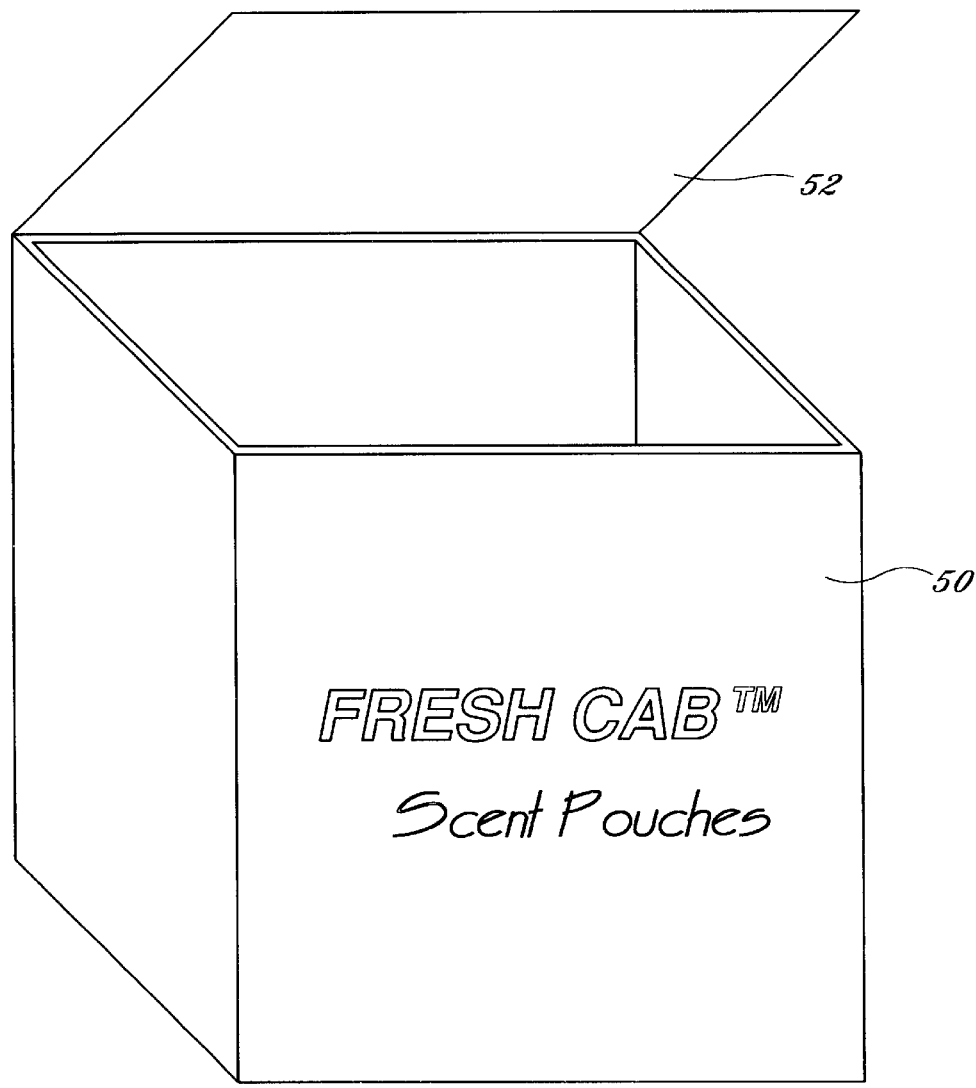
FIG. 4 is an upper perspective view.

A storage box 50 is also provided as shown in FIG. 4 of the drawings. The storage box 50 is capable of storing a plurality of containers 20 filled with the material 40. Preferably an impermeable bag receives the plurality of containers 20 during storage for preventing the evaporation of the fragrance oil. A lid 52 pivotally attached to the storage box 50 allows selective closing by the user during non-use.

In use, the user removes at least one container 20 from the storage box 50. The user ensures that the drawstring 30 has the opening 24 completely closed to prevent removal of the material 40. The fragrance oil within the material 40 is slowly emitted from within the container 20. The scent irritates the respiratory system of rodents 14 and small animals thereby forcing them away from the vehicle 12. The fragrance oil also provides a pleasant scent for the user within the vehicle 12. After the scent is weakened over time, the user simply removes the old container 20 and attaches a new container 20.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A method of repelling rodents comprising the steps of:
    (a) providing a permeable container having a volume of corn cob chips permeated with a volume of Canadian wilderness fragrance oil comprised of linalool 90, eucalyptus 80/85, rosemary Spanish, patchouli, turpentine rectified, caryophellene B, acetaldehyde, aldehyde C-14, fir balsam anhydrol, linalyl acetate special, dioctyl adipate, cis 3 hexenyl acetate, mousse de chene, hydroxy citronellal, iso borneol acetate, neryl acetate, fir balsam, viridine, fir needle Canadian, galaxolide 50, musk ketone, boreol leavo, hercolyn D, benzyl salicylate, camphor gum, grapefruit white, sage clary, mousse de arbre, styrallyl alcohol, vertenex, cedarwood Texas white, lemon California, veltol plus and fenchyl alcohol alpha; and (b) positioning said permeable container within an enclosed structure desired to be protected from the presence of rodents.

* * * * *